(12) United States Patent
Thomas et al.

(10) Patent No.: US 11,911,068 B2
(45) Date of Patent: Feb. 27, 2024

(54) POSITIONING DEVICE FOR MEDICAL DEVICES

(71) Applicant: Smart Biomedical Corporation, Kingston (CA)

(72) Inventors: Sumesh Thomas, Calgary (CA); ChunMin Chee, Calgary (CA); Wiley Chung, Kingston (CA)

(73) Assignee: Smart Biomedical Corporation, Kingston (CA)

( * ) Notice: Subject to any disclaimer, the term of this patent is extended or adjusted under 35 U.S.C. 154(b) by 906 days.

(21) Appl. No.: 16/478,571

(22) PCT Filed: Jan. 16, 2018

(86) PCT No.: PCT/CA2018/050039
§ 371 (c)(1),
(2) Date: Jul. 17, 2019

(87) PCT Pub. No.: WO2018/132898
PCT Pub. Date: Jul. 26, 2018

(65) Prior Publication Data
US 2019/0336164 A1    Nov. 7, 2019

Related U.S. Application Data

(60) Provisional application No. 62/447,113, filed on Jan. 17, 2017.

(51) Int. Cl.
*A61B 17/34* (2006.01)
*A61M 39/02* (2006.01)
*A61B 17/00* (2006.01)

(52) U.S. Cl.
CPC ...... *A61B 17/3415* (2013.01); *A61B 17/3421* (2013.01); *A61M 39/02* (2013.01);
(Continued)

(58) Field of Classification Search
CPC ............ A61B 17/3415; A61B 17/3421; A61B 17/3494; A61B 2017/3458;
(Continued)

(56) References Cited

U.S. PATENT DOCUMENTS 1,248,492 A * 12/1917 Hill .................. A61B 17/34
604/165.02
4,356,826 A * 11/1982 Kubota ............. A61B 17/3494
604/117
(Continued)

FOREIGN PATENT DOCUMENTS

CN    203001082 U    6/2013
CN    203852412 U    10/2014
(Continued)

OTHER PUBLICATIONS

Ball et al., "Chest Tube Complications: How Well Are We Training Our Residents?," Canadian Journal of Surgery, Apr. 2006, vol. 50(6), pp. 450-458.
(Continued)

*Primary Examiner* — Kathleen S Holwerda
(74) *Attorney, Agent, or Firm* — Angela Lyon

(57) ABSTRACT

The present disclosure is directed to a positioning device for insertion into a patient. The device includes an outer sheath having an external thread on an outer surface. The device also includes a removable inner cannula for insertion into the outer sheath. The cannula has a penetrating end at its insertion end. It may also include a locking device for locking the inner cannula to the outer sheath. The device may be a pneumothorax drainage device.

19 Claims, 3 Drawing Sheets

(52) U.S. Cl.
CPC ........... *A61B 2017/00026* (2013.01); *A61B 2017/00809* (2013.01); *A61B 2017/347* (2013.01); *A61B 2017/3458* (2013.01)

(58) Field of Classification Search
CPC ........ A61B 2017/347; A61B 2017/349; A61B 2017/00026; A61B 2017/00809; A61M 1/04; A61M 1/84; A61M 2039/0276; A61M 39/02
See application file for complete search history.

(56) References Cited

U.S. PATENT DOCUMENTS

| | | | |
|---|---|---|---|
| 4,813,941 A | | 3/1989 | Shea |
| 5,258,003 A | * | 11/1993 | Ciaglia ............ A61B 17/3417 604/164.11 |
| 5,419,776 A | | 5/1995 | Baer |
| 5,735,867 A | * | 4/1998 | Golser ............... A61M 25/065 604/164.11 |
| 6,330,882 B1 | | 12/2001 | French |
| 6,517,519 B1 | * | 2/2003 | Rosen ............... A61B 17/3415 606/167 |
| 6,595,928 B2 | | 7/2003 | Mansy et al. |
| 7,135,010 B2 | | 11/2006 | Buckman et al. |
| 7,229,433 B2 | | 6/2007 | Mullen |
| 7,499,745 B2 | | 3/2009 | Littrup et al. |
| 2002/0198554 A1 | * | 12/2002 | Whitman ........... A61B 17/3476 606/167 |
| 2004/0039400 A1 | * | 2/2004 | Schmieding ....... A61B 17/0281 606/108 |
| 2005/0288566 A1 | | 12/2005 | Levendusky et al. |
| 2008/0119846 A1 | | 5/2008 | Rioux |
| 2008/0249467 A1 | * | 10/2008 | Burnett ................. A61B 1/313 604/117 |
| 2010/0113963 A1 | | 5/2010 | Smits et al. |
| 2012/0018950 A1 | | 1/2012 | Kingsley |
| 2016/0067391 A1 | | 3/2016 | Real et al. |

FOREIGN PATENT DOCUMENTS

| | | |
|---|---|---|
| CN | 105496517 A | 4/2016 |
| DE | 202007009361 U1 | 12/2007 |
| DE | 102009028257 A1 | 2/2010 |

OTHER PUBLICATIONS

Currie et al., "Pneumothorax: An Update," Postgrad Medical Journal, Feb. 2007, vol. 83(981), pp. 461-465.

Frost and Sullivan "Report on Innovations in Battlefield Medicine" TechVision Opportunity Engine, Jul. 2016, 18 pages.

Hodgetts et al., "Operational Mortality of UK Service Personnel in Iraq and Afghanistan: A One Year Analysis 2006-2007," Journal of the Royal Army Medical Corps, Dec. 2007, vol. 153(4), pp. 252-254.

International Patent Application No. PCT/CA2018/050039, International Search Report and Written Opinion dated Apr. 4, 2018.

Macduff et al., "Management of Spontaneous Pneumothorax: British Thoracic Society Pleural Disease Guideline 2010," Thorax, Mar. 2010, vol. 65(2), pp. ii18-ii31.

Melton et al., "Incidence of Spontaneous Pneumothorax in Olmsted County, Minnesota: 1950 to 1974," American Review of Respiratory Diseases, Jun. 1979, vol. 120(6), 1379-1382.

Morrison et al., "Is Pre-Hospital Thoracotomy Necessary in the Military Environment?," Injury, May 2011, vol. 42 (5), pp. 469-473.

Seldinger., "Catheter Replacement of the Needle in Percutaneous Arteriography; A New Technique," Acta Radiologica, Oct. 1952, vol. 39(5), pp. 368-376.

* cited by examiner

POSITIONING DEVICE FOR MEDICAL DEVICES

CROSS REFERENCE TO RELATED APPLICATION

This application claim priority to U.S. Ser. No. 62/447,113, filed on Jan. 17, 2017, the entire contents of which is hereby incorporated by reference.

FIELD

The present disclosure relates generally to devices and methods for the proper positioning of medical devices in a patient, and more particularly, to a pneumothorax drainage device.

BACKGROUND

Spontaneous pneumothorax is a significant global health problem with an estimated incidence of 7-37/100,000 people per year[1,2] or up to 2 million events per year globally. Air in the chest cavity can sometimes resolve itself but often requires a hospital admission and more importantly, lifesaving urgent medical care. In the military combat setting, about 13% of penetrating wounds to the thoracic cavity require thoracic intervention including a chest tube[5]. These thoracic injuries can contribute up to 30% of combat deaths[6].

The hallmark treatment of a symptomatic pneumothorax is the insertion of an intercostal drain however this skill is limited to health care practitioners with adequate training. The complication rate from chest tube insertion can be as high as 30%[3] including nerve injury, lung or other organ puncture, inadequate positioning, or infection. There is a desperate need to reduce complication rates and this can be achieved by a combination of better health care practitioner training and improving the insertion device and technique.

The conventional chest tube insertion technique, called 'surgical', involved an incision in the skin and blunt dissection of the chest wall until the health care practitioner penetrates the chest cavity and feels a loss of resistance. This is very operator dependent and can result in either under penetration (chest tube will not evacuate pneumothorax) or over penetration (puncture/laceration of organ). A finger sweep is performed to lessen the risk of laceration but as previously reported, the complication rates remain very high.

A newer technique involves the passage of the dilator and tube over a guidewire inserted via a needle. The modified Seldinger[4] technique simplifies the process for most but the initial insertion of the needle may also result in organ puncture. The operator needs to push/force the needle and dilator straight into the thoracic cavity and may overshoot the cavity into another organ. Examples of pneumothorax drainage devices may be found in U.S. Pat. Nos. 4,813,941; 7,229,433; and 6,330,882; and US Publication 2016/0067391. With these known devices, there is no method of finely adjusting the depth of the device except by forward pressure.

Similar problems exist when positioning other devices such as ports in a patient's abdomen, thorax, or joint spaces. It is desirable to be able to more accurately and easily position the devices into the patient.

It may be desirable to determine a change in the cavity that the device is inserted into as a means of determining the appropriate positioning of the device. This may be accomplished, for example, by detecting specific tissue or fluid. U.S. Pat. No. 7,499,745 discloses one example of a device that uses complex impedance measurements of tissue for the detection of medical pathologies. DE102009028257 discloses a recording and monitoring device for thorax impedance which uses a harmonic alternating current with three application electrodes. U.S. Pat. No. 6,595,928 discloses a device for detecting air cavities in humans and animals. US Publication 2005/0288566 discloses a device which uses impedance for placement of a needle and delivery of material through the needle to a desired location. US Publication 2012/0108950 discloses a method of guiding a catheter using impedance for intravascular detection and an ultrasound probe for visual guidance with the impedance.

It may therefore be desirable to provide a positioning device for positioning medical devices such as a pneumothorax drainage device to allow for depth control and/or cavity recognition in a patient.

SUMMARY

It is an object of the present disclosure to obviate or mitigate at least one disadvantage of previous systems.

In a first aspect, the present disclosure provides a positioning device for insertion into a patient. The positioning device has an outer sheath comprising a body and may include an external thread on an outer surface of the body. The device also has a removable inner cannula for insertion into the outer sheath. The cannula has a body for insertion in the body of the outer sheath and a penetrating end on the body of the cannula at an insertion end. The device may include a locking device for locking the inner cannula to the outer sheath.

In a further aspect, the device may be selected at a desired size to allow for the insertion of the device into a patient to the desired position. In a further aspect, the device may include a cavity detection system to detect one or more of tissue, air, and fluid.

In a further aspect, the present disclosure provides a method of inserting a positioning device into a patient. The method includes the step of inserting a removable inner cannula into an outer sheath. The outer sheath may have an external thread on an outer surface. The removable inner cannula may have a penetrating end at an insertion end. The method includes positioning the penetrating end at a desired location on a patient, and inserting the penetrating end into the patient. The method may include rotating the device so that the external thread moves the device into the patient. When the device is fully inserted, the inner cannula is removed from the outer sheath.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Generally, the present disclosure provides a method and positioning device for inserting the device into a patient with depth control and/or cavity recognition.

In one aspect, the positioning (or insertion) device has two parts, an outer sheath and an inner cannula. The inner cannula may be positioned in the outer sheath. These parts may be combined for insertion and separable once inserted in a desired position. The two parts may be locked together for insertion and may be unlocked for removal of the inner cannula.

The positioning device may include a system for depth control. The depth control may be achieved by helical threads on the outer sheath and a size of the outer sheath in accordance with the desired depth and position for the insertion of the intended medical device. For example, for insertion of a pneumothorax drainage device, the outer sheath size is selected taking into account the relevant parameters for positioning of the device. The helical threads on the outer sheath allow a user to insert the sheath into the chest cavity until the outer sheath is fully inserted. This may improve the positioning of the device to the required depth and lower the failure rate of insertion.

The positioning device may include a system for cavity recognition including the recognition of tissue, air, and fluid. Cavity recognition may be achieved using a number of systems such as for example electrical impedance systems. Such systems monitor the electrical impedance to detect where in the body cavity the device is located. Impedance signals change when the desired cavity is reached by the device. This change can be signaled to the operator for example by way of a light which changes colour when the impedance changes or numerically with a digital screen. Impedance detection may detect air and fluid. For example, it may detect air in the pleural space or it may be adjusted to detect pleural fluid. This system may be useful for a variety of applications, such as draining pleural effusions, chylothorax, empyemas, and hemothoraces. Sensitivity and threshold impedance may be altered for example to differentiate fluid, soft tissue (i.e., muscle and fat), and solid organs (i.e., liver, spleen, bowel, and lung).

The positioning device is described herein with reference to one example of positioning a pneumothorax drainage device. It may also be used for positioning other devices, for example, for minimally invasive surgery settings to aid in the safe port site placement in a patient, such as in the abdomen (laparoscopy), thorax (thoracoscopy) or joint spaces (arthroscopy).

Figure 1:
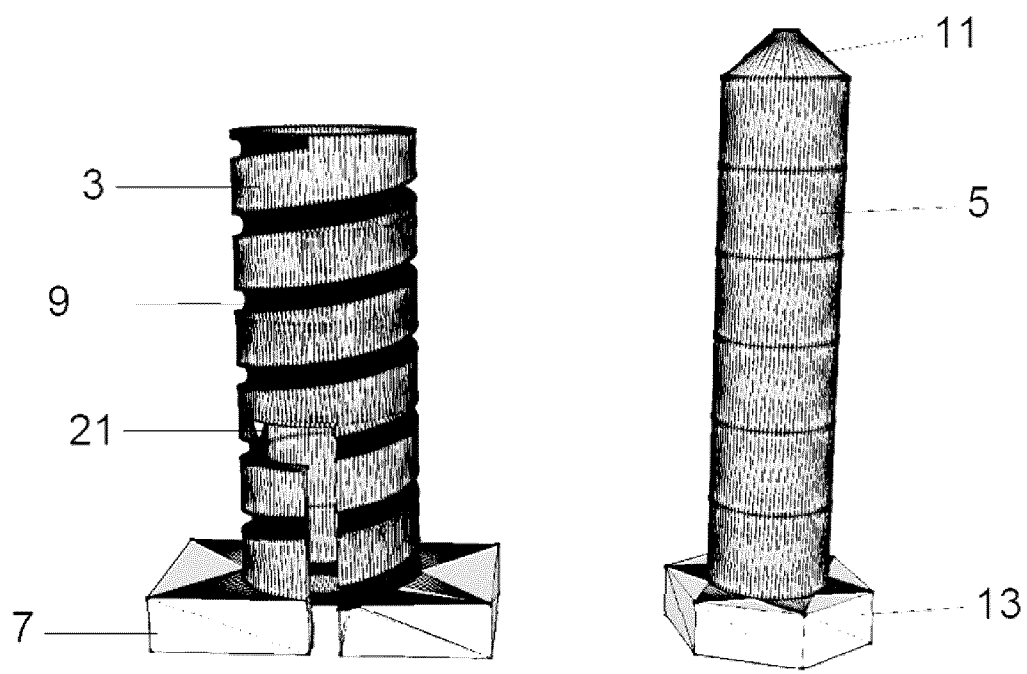
FIG. 1 shows one embodiment of the two part insertion apparatus having an outer sheath and inner cannula.

As shown in FIG. 1, in one embodiment, the insertion device 1 has two parts, an outer sheath 3 and an inner cannula 5. The outer sheath 3 may include a base flange 7 and external thread 9. The flange 7 may allow a user to apply insertion and rotational torque to the insertion device. The non-cutting external thread 9, when rotated clockwise, will direct the sheath forward while anti-clockwise rotation will direct the sheath backward. The angle, and pitch of the thread allows the user to have control of the depth of the penetrating tip 11 of device in a chest wall with inserting and rotational torque applied to the flange 7. The inner wall of the sheath may be smooth but may include a proximal locking port to lock the inner cannula to the outer sheath. The inner cannula and outer sheath may be locked together using any known systems.

The minimum diameter of the outer sheath is dictated by the diameter of the medical device to be inserted into the sheath. For example, for a pneumothorax drainage device, the minimum diameter of the outer sheath may be determined by the chest tube that will be placed within the sheath. Chest drains of 8 Fr size are the smallest used in neonatal practice (this equates to a minimum internal diameter of 3 mm) while larger bore accommodating sheaths would be required for pediatric and adult patients. The external diameter of the outer sheath is dependent on the strength of material used for the sheath and thread composition. The minimum external diameter is likely to be 1-2 mm greater than the internal diameter. The maximum diameter is dependent on the size of the patient and distance between rib spaces and depth of thread required for the size of patient. The diameter range is between 4 mm (newborn) and 25 mm (large animal).

The length of the outer sheath may be determined according to the positioning of the medical device for the intended purpose. For example, the length of the outer sheath for a pneumothorax drainage device may be dependent on the patient size and anticipated chest wall thickness. This can range from 5 mm (human newborn) to 100 mm (large animal). The inserting end of the outer sheath may be tapered to meet the penetrating tip of the inner cannula while the proximal end of the outer sheath abuts with the base flange. The base flange may be standardized to allow for adult finger grip and may have a diameter of 3-5 mm greater that the diameter of the outer sheath to avoid the risk of over-insertion.

The positioning device may include an inner cannula 5. The inner cannula may include a base 13 and a distal conical penetrating tip 11. The penetrating tip 11 may be a cutting tip or a non-cutting tip. The distal conical tip 11 penetrates the body cavity. This penetrating tip may consist of a non-cutting tip, for example for hospital use where initial skin break and exposure of intercostal tissue can be achieved with a scalpel. Alternatively, in another example, the penetrating tip 11 may be a cutting tip for field use where limited medical skill and/or surgical equipment are available. The surface of the cannula may be smooth.

The inner cannula and outer sheath may be locked together. Any known locking system may be used. In one aspect, the proximal end/base of the cannula is attached to the outer sheath by way of a locking channel 21. The inner cannula may be locked to the outer sheath by inserting a protrusion (not shown) on the outer surface of the inner cannula into a locking channel 21 in the outer sheath. As the inner cannula is inserted into the outer sheath, the protrusion moves through the longitudinal section of the channel until it reaches the end when the cannula is fully inserted. The cannula is then rotated so that the protrusion moves through the perpendicular section of the locking channel of the outer sheath. This prevents the inner cannula from being removed from the outer sheath until the cannula and/or sheath is rotated in the reverse direction, thereby moving the protrusion back to the longitudinal channel and moving the protrusion out of the longitudinal channel until the cannula is removed from the outer sheath.

Figure 2:
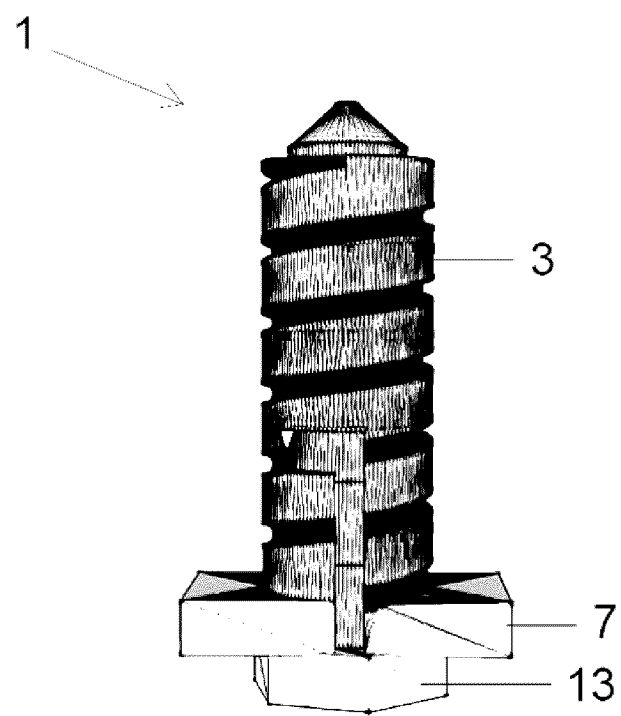
FIG. 2 shows the combined outer sheath and cannula of the two part insertion apparatus.

For insertion of the positioning device into a patient, the inner cannula is inserted into the outer sheath, as shown in FIG. 2. The outer diameter of the inner cannula is dependent on the diameter of the outer sheath. In some cases, the minimum diameter may be 3 mm and the maximum diameter may be variable, up to 25 mm. The length of the inner cannula may be dependent on the outer sheath. In some cases, it may extend 5 mm from the distal tip and 5 mm from the proximal base. The inserting end of the inner cannula may be designed with a tapering tissue cutting or non-cutting tip which protrudes just beyond the outer sheath while the proximal end may be housed within the outer sheath and may include a cavity recognition system such as a pressure and impedance micro-sensors manometer.

The device may include a cavity recognition system such as a system for monitoring electrical impedance. In one aspect, the outer sheath 3 may be comprised of conductive material to complete an electrical circuit to record impedance characteristics of tissue adjacent to the penetrating tip 11. Cavity detection may be housed in the inner cannula, for example using one of the following (but not exclusive) mechanisms:

Impedance detection. A small battery powers a low voltage circuit between the inner cannula and outer sheath, or between different terminals on the inner cannula. The electrical impedance of body tissue is measured between the separate terminals. The cavity of air is reached when the measured impedance decreases (electrical resistance increases) substantially.

Pressure detection. The outer sheath and inner cannula may be connected via a spring-loaded locking mechanism. When the two parts are joined and pressure is applied to the tip of the inner cannula, the spring is compressed. When pressure is released, the inner cannula is allowed to advance forward a set distance, signaling a loss of pressure.

Figure 3:
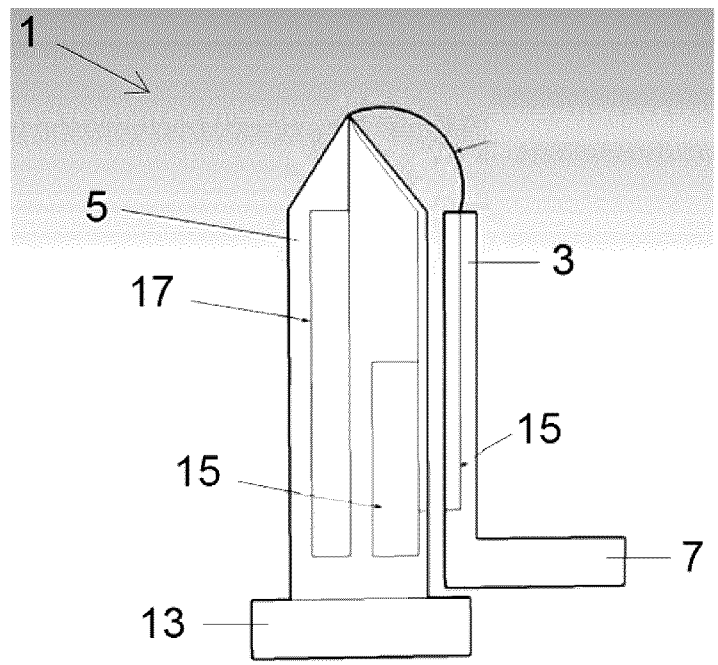
FIG. 3 shows the inner cannula with one embodiment of cavity detection and impedance detection systems.

FIG. 3 shows one example of the positioning device 1 with internal circuitry 15 between the inner cannula 5 and outer sheath 3 for measuring impedance between the cannula and the outer sheath. It also includes a pressure transducer or spring 17 to measure the cannula tip pressure.

Figure 4:
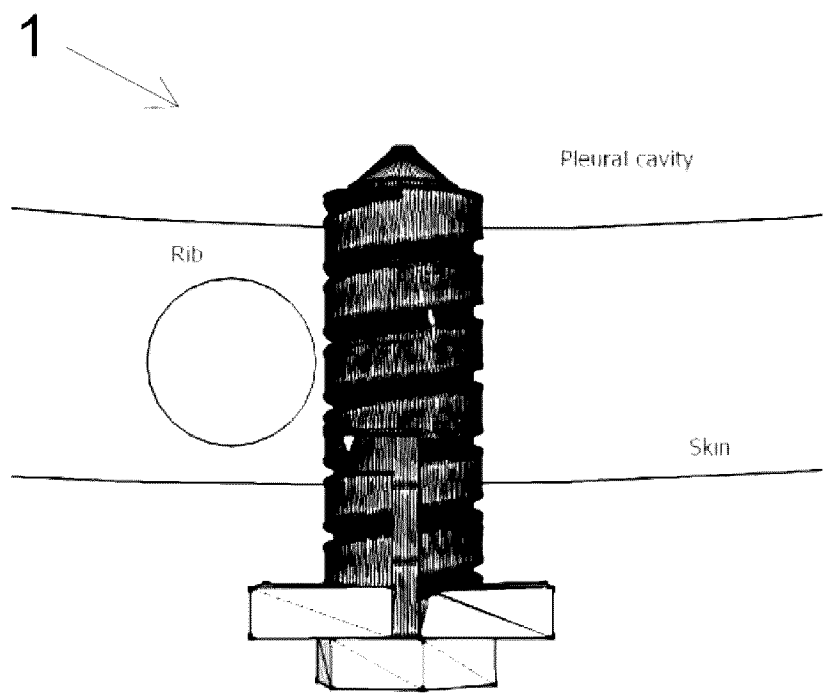
FIG. 4 shows the insertion of the combined two part insertion apparatus into a chest cavity.
Figure 5:
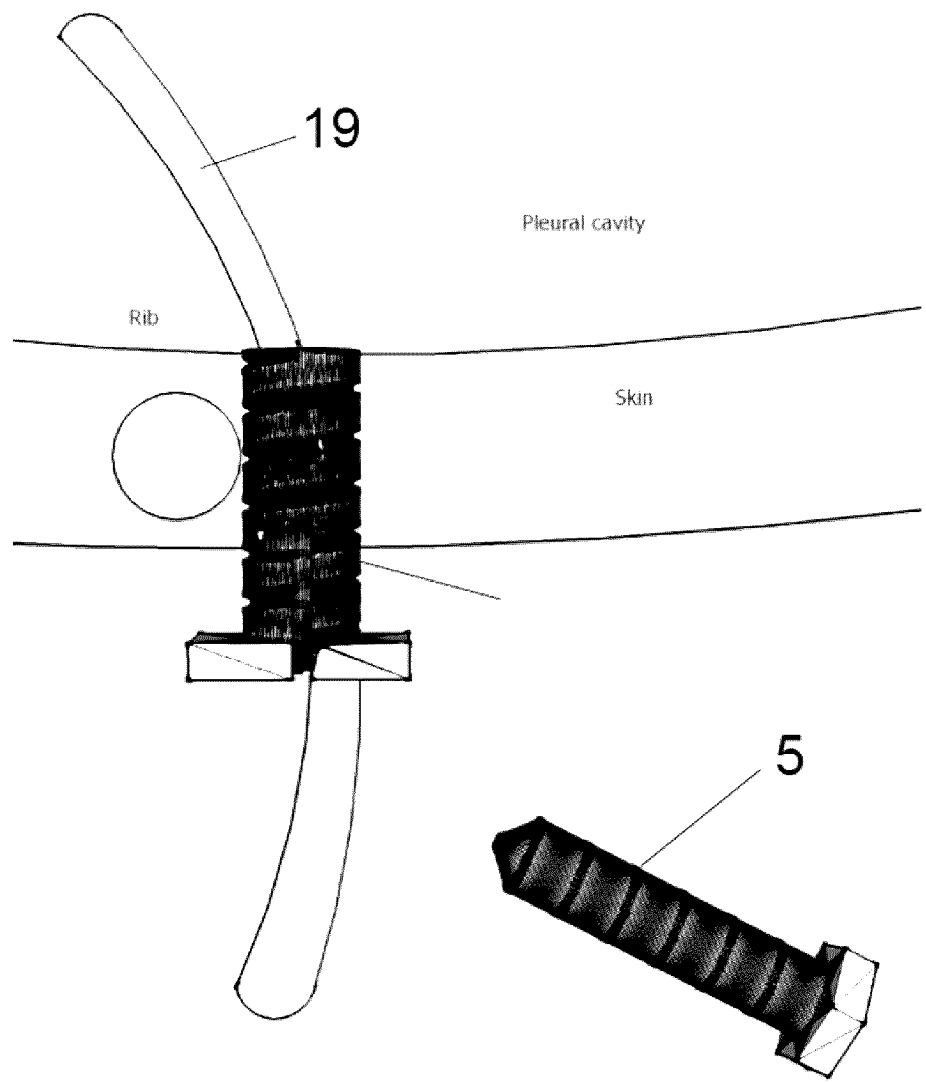
FIG. 5 shows the chest cavity with inserted outer sheath with inner cannula removed and a chest tube positioned in the outer sheath.

The positioning device may be inserted into a patient using one or more of the following steps. A positioning device may be selected depending on the relevant factors for the desired use, for example the appropriate size and penetrating end (i.e. cutting or non-cutting) may be selected. The inner cannula 5 may be inserted into the outer sheath 3 and the cannula and sheath locked together. The penetrating end 11 may be positioned at the appropriate position on a patient. The penetrating end 11 may be inserted into the patient. The positioning device 1 may be rotated with the external thread 9 inserting the device 1 into the patient. When the device 1 is fully inserted, the rotation is stopped. The inner cannula 5 may be unlocked from the outer sheath and removed. A medical device such as a drainage tube may be inserted into the outer sheath. FIG. 4 shows the inserted positioning device for pneumothorax drainage and FIG. 5 shows the device inserted in a patient with the inner cannula removed and a chest tube 19 inserted into the outer sheath 3.

In one aspect, the steps for inserting the positioning device are described using a pneumothorax drainage device:

1. Clinical decision about tube thoracotomy (chest tube insertion) is made by the operator, and insertion point is targeted rostral to the rib.
2. Appropriate anesthetic considerations are made including potential injection of local anesthetic to chest tube site where feasible.
3. Small incision is made in skin to penetrate sub-dermal layer.
4. Chest tube insertion apparatus (outer sheath and inner cannula combined) are inserted gently into skin incision.
5. With fingers wrapped around outer sheath flange, forward pressure is placed from base of apparatus and apparatus is twisted into chest wall with clockwise motion.
6. Once apparatus thread obtain purchase in chest wall, forward pressure is released but clockwise motion is continued.
7. The inner cannula sensor detects when apparatus is in chest wall (such as pressure-sensitive signal or impedance detection).
8. When inner cannula detects presence of pleural space (loss of pressure or drop in impedance) then inner cannula will signal user to halt advance of the penetrating device.
9. Inner cannula is detached and removed.
10. User inserts chest tube through outer sheath (which acts as placeholder for chest tube) and tube is attached to standard drainage device.
11. Once chest tube is inserted, outer sheath can be removed and drain secured or kept in place until patient is brought to a healthcare facility.

In the preceding description, for purposes of explanation, numerous details are set forth in order to provide a thorough understanding of the embodiments. However, it will be apparent to one skilled in the art that these specific details are not required. The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

REFERENCES

1. *Thorax* 2010; 65:ii18-ii31
2. Am Rev Respir Dis. 1979 December; 120(6):1379-82.
3. Can J Surg. 2007 December; 50(6): 450-458.
4. Seldinger S I (1953). "*Catheter replacement of the needle in percutaneous arteriography; a new technique*". Acta radiologica. 39 (5):368-76
5. Morrison J J, Mellor A, Midwinter M, Mahoney P, Clasper J C. Is pre-hospital thoracotomy necessary in the military environment? Injury. 2011; 42:469-473.
6. Hodgetts T, Davies S, Midwinter M, et al. Operational mortality of UK service personnel in Iraq and Afghanistan: a one year analysis 2006-2007. J R Army Med Corps. 2007; 153(4):252-254.

The invention claimed is:

1. A positioning device for insertion into a patient, comprising:
   a. an outer sheath having a wall and a longitudinal axis and comprising a body and an external thread having a root and a crest and running around the longitudinal axis on an outer surface of the body in a first direction;
   b. a removable inner cannula for insertion into the outer sheath, the cannula comprising a body for insertion in the body of the outer sheath, and a penetrating end on the body of the cannula at an insertion end;
   c. a locking device for locking the inner cannula to the outer sheath, the locking device comprising
      (i) a protrusion extending from the body of the inner cannula and
      (ii) a corresponding locking channel on the outer surface of the body of the outer sheath, the locking channel comprising a first section, the first section running parallel to the longitudinal axis, and a second section having a first end and a second end, the second section intersecting the first section at the first end and running from the first end to the second end in a direction perpendicular to the longitudinal axis and opposite to the first direction, the locking channel being cut through the full thickness of the wall of the outer sheath such that a portion of the root runs through the second section and the first end, wherein the first section of the locking channel runs through at least one portion of the root and at least one portion of the crest of the external thread; and d. a cavity detection system.

2. The positioning device of claim 1, wherein the outer sheath further comprises a base adjacent one end of the outer sheath body, the base having an outer diameter larger than an outer diameter of the outer sheath.

3. The positioning device of claim 1, wherein the inner cannula further comprises a base at an end of the cannula body opposite the penetrating end, the base having a diameter larger than an inner diameter of the body of the outer sheath.

4. The positioning device of claim 1, wherein the cavity detection system detects one or more of tissue, air, and fluid.

5. The positioning device of claim 1, wherein the cavity detection system comprises pressure detection, electrical resistance, or impedance detection.

6. The positioning device of claim 5, wherein the positioning device is a pneumothorax drainage device.

7. The positioning device of claim 5, wherein the cavity detection system is housed in the inner cannula.

8. The positioning device of claim 1, wherein the positioning device positions a pneumothorax drainage device.

9. The positioning device of claim 1, wherein the positioning device aids in safe port site placement in a patient.

10. The positioning device of claim 1, wherein the positioning device is configured for site placement in a patient's abdomen, thorax, or joint spaces.

11. The positioning device of claim 10, wherein the positioning device is configured for laparoscopy, thoracoscopy, or arthroscopy.

12. The positioning device of claim 11, wherein the positioning device is configured for draining pleural effusions, chylothorax, empyemas, or hemothoraces.

13. The positioning device of claim 1, wherein the external thread is a right-handed thread running clockwise around the longitudinal axis, and wherein the second section of the locking channel runs counter-clockwise.

14. A method of inserting a positioning device into a patient, comprising the steps of:
 a. providing the positioning device of claim 1;
 b. positioning the penetrating end at a desired location on a patient;
 c. inserting the penetrating end into the patient and rotating the positioning device so that the external thread moves the positioning device into the patient;
 d. when positioning device is fully inserted into the patient, cease rotating positioning device; and
 e. removing the inner cannula from the outer sheath
 wherein the step of inserting further comprises cavity detection.

15. The method of claim 14, further comprising the step of locking the inner cannula to the outer sheath.

16. The method of claim 14, wherein the cavity detection comprises pressure detection, electrical resistance, or impedance detection to detect one or more of air, fluid, or tissue.

17. The method of claim 16, wherein the cavity detection comprises differentiating fluid, soft tissue, and solid organs.

18. The method of claim 14, further comprising:
 f. inserting a drainage tube into the outer sheath.

19. The method of claim 18, wherein the drainage tube is a chest tube.

* * * * *